(12) United States Patent
Walsh et al.

(10) Patent No.: US 7,022,872 B2
(45) Date of Patent: Apr. 4, 2006

(54) METHOD FOR MAKING FLUORINE LABELED L-DOPA

(75) Inventors: Joseph C. Walsh, Pacific Palisades, CA (US); Henry C. Padgett, Hermosa Beach, CA (US)

(73) Assignee: Molecular Technologies, Inc., Culver City, CA (US)

( * ) Notice: Subject to any disclaimer, the term of this patent is extended or adjusted under 35 U.S.C. 154(b) by 0 days.

(21) Appl. No.: 10/742,023

(22) Filed: Dec. 19, 2003

(65) Prior Publication Data

US 2005/0137421 A1   Jun. 23, 2005

(51) Int. Cl.
*C07C 229/36* (2006.01)
*C07C 271/22* (2006.01)

(52) U.S. Cl. .......................... 560/39; 560/29
(58) Field of Classification Search .................... 560/8, 560/19, 205, 29, 39
See application file for complete search history.

(56) References Cited

U.S. PATENT DOCUMENTS

| | | | |
|---|---|---|---|
| 3,023,235 A | 2/1962 | Leonard | |
| 3,859,331 A | 1/1975 | Kaiser et al. | |
| 3,969,397 A | 7/1976 | Kaiser et al. | |
| 4,005,127 A | 1/1977 | Knowles et al. | |
| 4,440,936 A | 4/1984 | Riley | |
| 4,716,246 A | 12/1987 | Reinhold et al. | |
| 4,879,398 A | 11/1989 | Getman et al. | |
| 5,393,908 A | 2/1995 | Satyamurthy et al. | |
| 5,510,522 A | 4/1996 | Satyamurthy et al. | |
| 5,658,943 A | 8/1997 | Berryman et al. | |

OTHER PUBLICATIONS

Deng et al, Tetrahedron Asymmetry 13 (2002) 1135-1140.*

CA accession No. 2002:402772 for Konkel et al, for Journal of Fluorine Chemistry (2002) 115(1) pp. 27-32.*
CA accession No. 2000:177130 for Brown, Tetrahedron Letters (2000) 41(10) pp. 1623-1626.*
CA accession No. 1992:255995 for Nie et al, Journal of Fluorine Chemistry (1991) 55(3), 259-269.*
CA accession No. 1991:116927 for Bakos et al, Hungarian Patent 47203 (1998).*
CA accession No. 1935:41892 for Oliverio, Gazzetta Chimca Italiana (1935) 65, 143-152.*
Dolle et al., "6-[$^{18}$F]Fluoro-L-DOPA by Radioflurodestannylation: A Short And Simple Synthesis Of A New Labeling Precursor," *Journal of Labelled Compunds And Radiopharmaceuticals*, vol. XLI, No. 2, pp. 105-114, (1998).
Deng et al., "Convenient Syntheses of 2-, 5- and 6-Fluoro- and 2,6-Difluoro-L-DOPA," *Tetrahedron: Asymmetry*, 13, pp. 1135-1140, (2002).
Namavari et al., "Regioselective Radiofluorodestannylation With [$^{18}$F]F$_2$ and [$^{18}$F]CH$_3$COOF: A High Yield Synthesis of 6-[$^{18}$F]Fluoro-L-DOPA," *Appl. Radiat. Isot.*, vol. 43, No. 8, pp. 989-996, (1992).
Guzel et al., "Synthesis And Characterization Of {[(COD)Rh(Bis-(2R,3R)-2,5- Diethylphospholanobenzene)] +BARF$^-$} For Use In Homogeneous Catalysis In Supercritical Carbon Dioxide," *Inorganica Chimica Acta*, 325, pp. 45-50 (2001).

* cited by examiner

*Primary Examiner*—Bernard Dentz

(57) ABSTRACT

The invention relates to a method for preparing F-Dopa and $^{18}$F-Dopa and intermediates that are useful in the method. The invention is a method that synthesizes F-Dopa and $^{18}$F-Dopa in good yield with high enantiopurity without the need for further transformations. The method includes the step of reacting a benzaldehyde derivative with a phosphonic acid derivative to produces an olefin intermediate that can be asymmetrically hydrogenated to produce the desired enantiomer.

6 Claims, 2 Drawing Sheets

METHOD FOR MAKING FLUORINE LABELED L-DOPA

BACKGROUND OF THE INVENTION

Positron emission tomography (PET) is a diagnostic imaging technique for measuring the metabolic activity of cells in the human body. PET can show images of blood flow, glucose metabolism in the brain, or rapid changes in activity in various areas of the body. It can be used to show changes in physiology before any change in gross anatomy has occurred. PET has been used in diagnosing diseases such as cancer, heart disease, Alzheimer's disease, Parkinson's disease, and schizophrenia.

PET uses chemical compounds that are labeled with radioactive atoms that decay by emitting positrons. The most commonly used PET radioisotopes are $^{11}C$, $^{13}N$, $^{15}O$, and $^{18}F$. Typically, the labeled compound is a natural substrate, substrate analog, or drug that is labeled with a radioisotope without altering the compound's chemical or biological properties. After injection into the tissue, the radiolabeled compound should follow the normal metabolic pathway of its unlabeled counterpart. The labeled compound emits positrons as it moves through the tissue. Collisions between the positrons and electrons that are present in the tissue emit gamma rays that are detectable by a PET scanner.

3,4-dihydroxyphenyl-L-alanine (L-Dopa) is the precursor for the neurotransmitter dopamine. L-Dopa is transported to the brain and is picked up by the nerve cells that produce dopamine. Once there, L-Dopa is converted into dopamine for the nerve cells to use as a neurotransmitter.

$^{18}F$-labeled PET tracers have been used clinically in the study and diagnosis of brain abnormalities. In particular, 3,4-dihydroxy-6-[$^{18}F$]fluoro-L-phenyl alanine ($^{18}F$-Dopa) is a radiolabeled analog of L-Dopa that has been used in neurology to study metabolism, neurotransmission, and cell processes. $^{18}F$-Dopa is a PET tracer that is used to analyze the presynaptic domaine function in animals and humans. Clinical diagnosis of Parkinson's disease and other biological disorders are easily determined via synaptic uptake of $^{18}F$-Dopa into various regions of the brain. 3,4-dihydroxy-6-fluoro-L-phenyl alanine (F-Dopa) is an analytical standard that is useful in the evaluation of $^{18}F$-Dopa compounds. Clinical use of $^{18}F$-Dopa has steadily increased resulting in a need to provide quicker and more efficient methods of its production.

Typical methods of preparing F-Dopa and $^{18}F$-Dopa result in racemic (d,l) mixtures that often require additional steps to isolate the L-enantiomer. Other methods avoid the need to resolve the enantiomers by starting with L-Dopa or L-3,4-dimethoxyphenyl alanine. Although these methods do not require additional steps to isolate the desired L-enantiomer, they have disadvantages that affect yield and efficiency.

Thus, there still exists a need for a method of preparing F-Dopa and $^{18}F$-Dopa in which the desired enantiomer can selectively be produced in high yield with high optical purity in a short number of synthetic steps without the need for extensive resolution.

BRIEF SUMMARY OF THE INVENTION

The invention is a method that is useful for preparing L-Dopa analogs, such as F-Dopa and $^{18}F$-Dopa. The method uses a novel olefin intermediate. The olefin intermediate can be stereoselectively hydrogenated to produce the desired enantiomer in high optical purity. Typically, the olefin is stereoselectively hydrogenated with a chiral catalyst that asymmetrically adds hydrogen across the double bond.

Typically, the synthesis begins by reacting a benzaldehyde derivative with a phosphonic acid derivative to produce the following olefin intermediate:

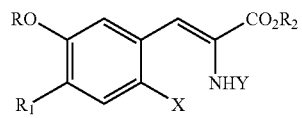

wherein R is typically hydrogen or a hydroxyl protecting group; $R_1$ is typically hydrogen or —O—R; $R_2$ is a carboxylic protecting group; Y is an amine protecting group; and X is hydrogen, halogen, nitro, amino, stannyl, silyl, thio, phosphoryl, boryl or oxo group.

The olefin intermediate can be stereoselectively hydrogenated with a catalyst to produce either the R or S enantiomer. In the next step, the protecting groups can be removed to afford the desired product.

The method can be used to prepare L-Dopa analogs in a minimum number of steps. The hydrogenation step increases yield and efficiency because a catalyst can be chosen that will produce the desired enantiomer. Thus, the invention provides an efficient and economical method for preparing L-Dopa analogs.

The synthesis of F-Dopa can begin with reacting 3,4-dimethoxybenzaldehyde derivative with tert-Butoxycarbonylamino-(dimethoxy-phosphoryl)-acetic acid ethyl ester to produce an intermediate having the following formula:

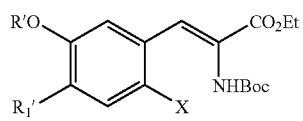

wherein R' is a hydroxyl protecting group; $R_1$' is —O—R'; and X is halogen, such as fluorine. The intermediate contains an olefin that can be stereoselectively hydrogenated with a catalyst to produce either the S or R enantiomer. After the intermediate is hydrogenated, the hydroxyl and amine protecting groups are removed to afford F-Dopa.

The synthesis of $^{18}F$-Dopa follows a similar reaction scheme. In the preparation of $^{18}F$-Dopa, 3,4-dimethoxy-6-iodobenzaldehyde is reacted with tert-Butoxycarbonylamino-(dimethoxy-phosphoryl)-acetic acid ethyl ester to produce the intermediate containing an olefin. The intermediate is stereoselectively hydrogenated with a catalyst. The 3,4-methyl groups are removed, and the phenols are then protected with di-tert-butyl-dicarbonate ($Boc_2O$) or 2-tert-Butoxycarbonyloxyimino-2-phenylcetonitrile (Boc-On). The halogen at the 5-position, typically an iodine atom, is then replaced with a tin moiety to produce the $^{18}F$-Dopa precursor:

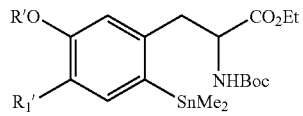

wherein R' is a hydroxyl protecting group, and $R_1'$ is —O—R'.

The precursor is fluoro-destannylated and the protecting groups are removed to produce $^{18}$F-Dopa.

This method prepares F-Dopa and $^{18}$F-Dopa in minimal number of steps and does not require additional steps to isolate the desired enantiomer. The resulting product is produced in good yield with high optical purity.

BRIEF DESCRIPTION OF THE SEVERAL VIEWS OF THE DRAWING(S)

Having thus described the invention in general terms, reference will now be made to the accompanying drawings wherein:

The invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

DETAILED DESCRIPTION OF THE INVENTION

The invention is a process for preparing L-Dopa analogs, and in particular, F-Dopa and $^{18}$F-Dopa in a short number of steps without the need for extensive resolution. The process includes the step of reacting a benzaldehyde derivative with a phosphonic acid derivative to produce an intermediate having an olefin moiety. The olefin can be stereoselectively hydrogenated with a chiral catalyst and hydrogen gas to produce the desired enantiomer.

Figure 1:
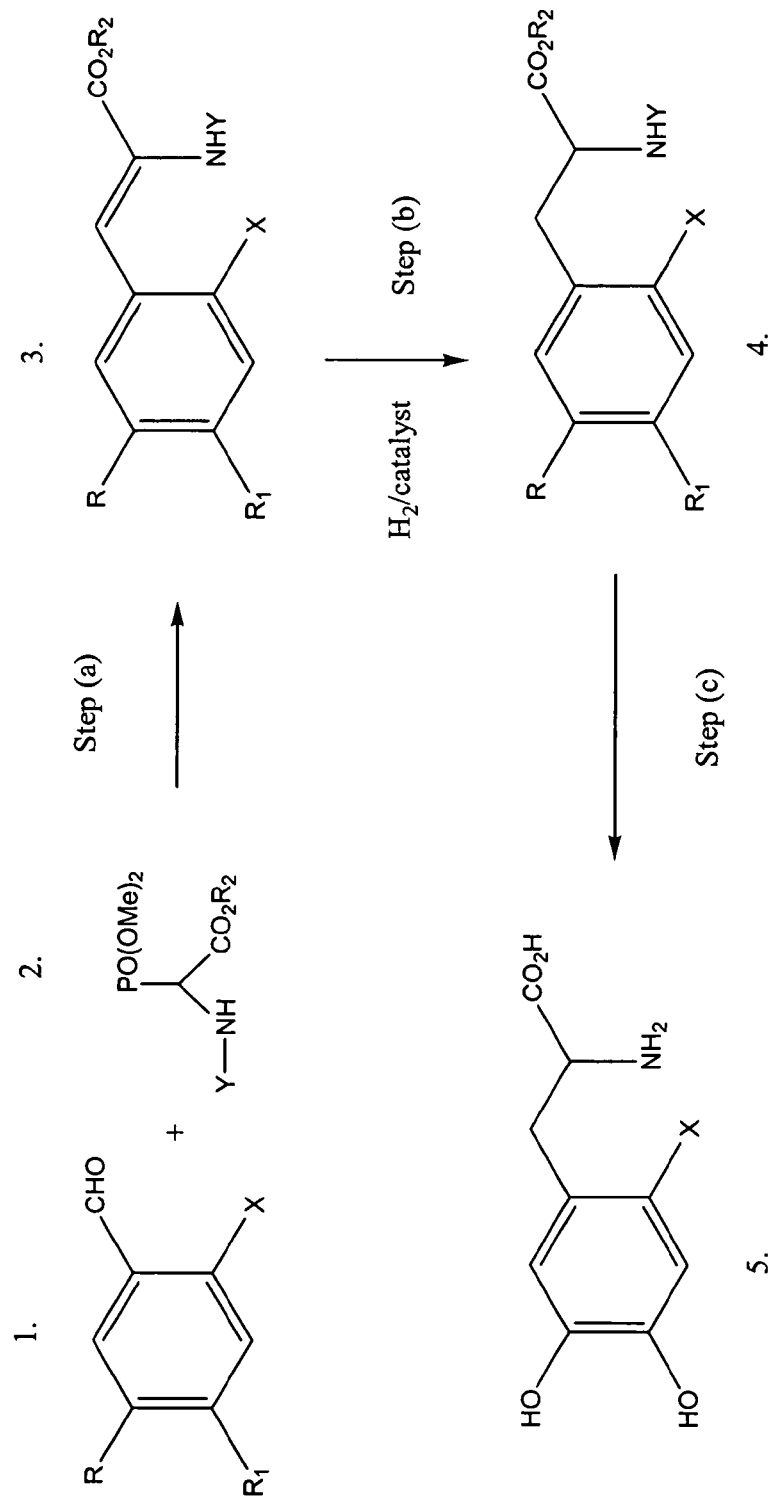
FIG. 1 illustrates a reaction scheme for preparing F-Dopa.

The synthesis of L-Dopa analogs begins with reacting a benzaldeyde derivative with a phosphonic acid derivative to produce an intermediate having an olefin moiety. As illustrated in FIG. 1, the synthesis includes the steps of:

(a) reacting compound 1 with compound 2 to produce an intermediate having an olefin (compound 3);

(b) stereoselectively hydrogenating the olefin to produce compound 4; and (c) optionally, deprotecting the hydroxyl, carboxylic, and amine moieties.

As shown in FIG. 1, the process begins with reacting a benzaldehyde derivative with a phosphonic acid derivative to produce an olefin intermediate according to the following reaction scheme:

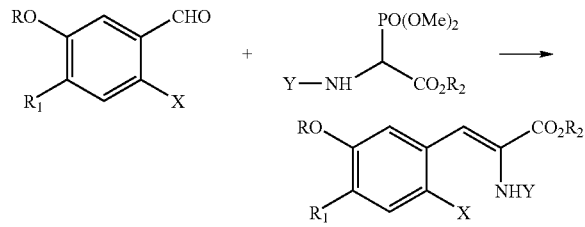

wherein:

R is hydrogen or a hydroxyl protecting group;
$R_1$ is hydrogen or —O—R;
X is hydrogen, halogen, nitro, amino, stannyl, silyl, thio, phosphoryl, boryl or oxo group;
$R_2$ is a carboxylic acid protecting group; and
Y is an amine protecting group.

Reaction step (a) typically takes place in a polar aprotic solvent under an inert atmosphere. Suitable solvents include, without limitation, chloroform ($CHCl_3$), methylene chloride ($CH_2Cl_2$), tetrahydrofuran (THF), acetonitrile ($CH_3CN$), N,N-dimethyl formamide (DMF), and N-methyl pyrrolidine (NMP).

After reaction step (a) is complete, the olefin intermediate 3 is treated with a chiral catalyst and hydrogen gas to asymmetrically add hydrogen across the double bond and produce the desired enantiomer. Reaction step (b) is illustrated in the following reaction scheme:

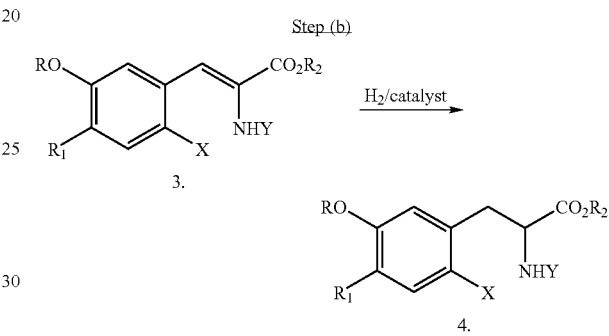

wherein R, $R_1$, $R_2$, X and Y are the same as defined above. Reaction step (b) is typically carried out in THF, methanol, (MeOH), ethanol (EtOH), ethyl acetate (EtOAc), $CH_2Cl_2$, and mixtures and blends thereof.

In optional reaction step (c), any protecting groups that are present can be removed to produce the final product:

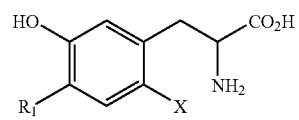

wherein $R_1$ and X are the same as defined above. Typically, the protecting groups are removed by treating compound 4 with a reagent that is suitable for removing a particular protecting group. Suitable reagents include, without limitation, hydrobromic acid (HBr), hydroiodic acid (HI), boron tribromide ($BBr_3$), and trimethylsilyliodide (TMSI).

In a preferred method of preparing F-Dopa, 2-fluoro-4,5-dimethoxybenzaldehyde is reacted with tert-Butoxycarbonylamino-(dimethoxy-phosphoryl)-acetic acid ethyl ester to produce 2-tert-butoxycarbonylamino-3-(2-fluoro-4,5-dimethoxy-phenyl)-acrylic acid ethyl ester. In this method R is methyl, $R_1$ is methoxy, X is fluorine, $R_2$ is methyl, and Y is tert-butoxycarbonyl.

Figure 2:
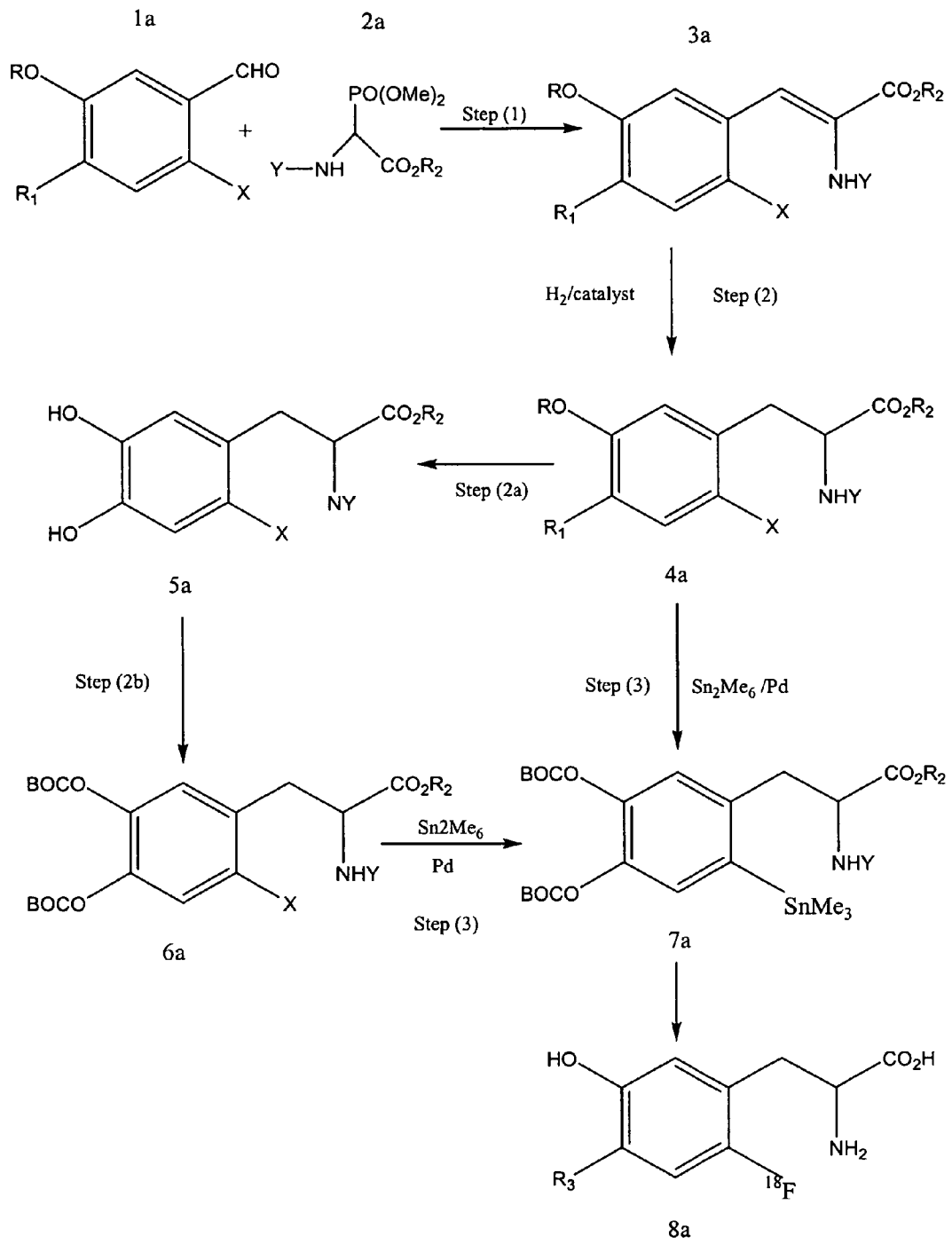
FIG. 2 illustrates a reaction scheme for preparing $^{18}$F-Dopa and its related precursor.

[$^{18}$F]Fluoro-labeled L-Dopa and a related precursor can also be prepared using the method of the invention. The synthesis of $^{18}$F-Dopa is illustrated in FIG. 2. Similar to the process for preparing F-Dopa, the synthesis begins by treating a benzaldehyde derivative with a phosphonic acid derivative to produce an olefin intermediate.

With reference to FIG. 2, the synthesis of $^{18}$F-Dopa begins with the reaction of compound 1a with compound 2a, wherein R, $R_1$, $R_2$, and Y are the same as defined above, and X is halogen. As illustrated in FIG. 2, the synthesis includes the following steps:

(1) reacting compound 1a with compound 2a to produce an intermediate having an olefin (3a);

(2) asymmetrically hydrogenating the olefin to produce compound 4a;

(3) stannylating compound 4a to produce the $^{18}$F-Dopa precursor (7a); and (4) optionally, radiolabeling the precursor to produce $^{18}$F-Dopa (8a).

Typically, the synthesis of $^{18}$F-Dopa begins with a commercially available benzaldehyde derivative such as 3,4-dimethoxy-6-iodobenzaldehyde. Other commercially available iodobenzaldehyde derivatives having different alkoxy groups can be used. Typical examples include, without limitation, ethoxy, benzyloxy, and allyoxy.

If a benzaldehyde derivative having protecting groups other than tert-butoxycarbonyl ("Boc") is used as the starting material it may be desirable to hydrolyze the group(s) and reprotect them with Boc. It has been found that Boc is an excellent protecting group that facilitates fluoro-destannylation and the final hydrolysis after the fluorination step. It should be recognized that other protecting groups can be used in place of Boc, although not necessarily with equivalent results. Other suitable protecting groups that can be used in place of Boc include, without limitation, carbamates, and in particular, moieties containing carbonyl groups.

With reference to FIG. 2, a reaction scheme is shown that includes the alternative steps of hydrolyzing the methoxy groups and reprotecting them with Boc. As illustrated in FIG. 2, the reaction scheme further includes the steps of:

(2a) removing any alkyl or benzyl moieties from each R and $R_1$; and (2b) reprotecting the phenol groups.

In the final step of preparing the $^{18}$F-Dopa precursor, the reaction product of step 2 is treated with a stannylating agent, such as hexamethylditin, to produce the $^{18}$F-Dopa precursor.

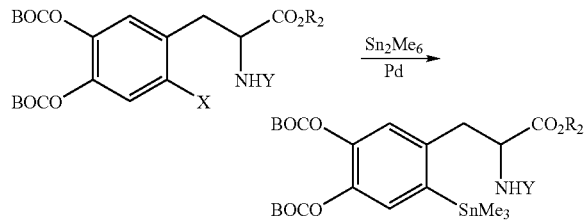

The resulting precursor is shelf stable at room temperature and reacts quickly with [$^{18}$F]CH$_3$COOF, [$^{18}$F]F$_2$, or [$^{18}$F]OF$_2$, or mixtures thereof to produce $^{18}$F-Dopa in hig yield that can be injected into a patient and tracked with PET. A preferred $^{18}$F-Dopa precursor is shown below:

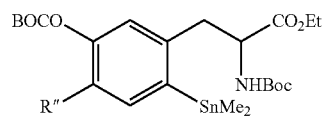

wherein R" is hydrogen or —O-Boc.

Typically, the precursor is fluoro-destannylated on site or at a location that is close to the PET facilities. $^{18}$F-Dopa is prepared by bubbling [$^{18}$F]CH$_3$COOF, [$^{18}$F]F$_2$, or [$^{18}$F]OF$_2$ through the precursor and treating the resultant product with HBr followed by partial neutralization with sodium hydroxide (NaOH) (Namavari, M., et al., *Appl. Radiat. Isot.*, 1992, 43 989–996). Other reagents may be used to hydrolyze the final product, such as HI, BBr$_3$, TMSI, or HBr in acetic acid. The final product has the following formula:

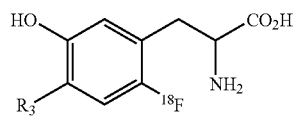

wherein $R_3$ is hydrogen or a hydroxyl group. The method for preparing $^{18}$F-Dopa is efficient and is carried out in a minimum number of steps, and produces $^{18}$F-Dopa in good yield with high optical purity.

Hydroxyl and carboxylic protecting groups that are useful in the invention must fulfill a number of requirements. The protecting groups should react selectively in good yield to give a protected substrate that is stable for future reactions. The protecting groups should be able to be selectively removed in good yield at the end of the reaction scheme or at any other time that is appropriate. Suitable protecting groups should also prevent unwanted reactions towards the hydroxyl group (or in the case of $R_2$, towards the carboxylic group), should not be affected by reaction conditions, and should not interfere with reactions on other portions of the molecule. It is also desirable that the protecting groups will help enhance reactions by increasing yield or selectivity.

Exemplary hydroxyl protecting groups include, without limitation, alkyl, alkyl ether and alkyl thioethers $C_1-C_{10}$ including, without limitation, methyl, isopropyl, t-butyl, methoxymethyl, benzyloxymethyl, methoxyethoxymethyl, methylthiomethyl, phenylthiomethyl, azidomethyl, cyanomethyl, and 1-ethoxyethyl; cyclic alkanes and ethers $C_3-C_{10}$ including, without limitation, tetrahydropyranyl, cyclopropylmethyl, and cyclohexyl; vinylic $C_2-C_5$, allylic $C_2-C_5$ including, without limitation, allyl, propargylic $C_2-C_5$ including propargyl and alkynic $C_2-C_5$; substituted phenyl, substituted benzyl, and substituted aryl groups including, without limitation, benzyloxymethyl, phenylthiomethyl, phenacyl, benzyl, 2,6-dimethylbenzyl, 4-methoxybenzyl, o-nitrobenzyl, 4-(dimethylamino)carbonylbenzyl, 4-methylsulfinylbenzyl, 9-anthrylmethyl, 4-picolyl, and mono to multiply substituted arenes with halo, nitro, or amino groups; ester groups including, without limitation, acetate, levulinate, pivaloate, benzoate, 9-fluorenecarboxylate, and xanthenecarboxylate; carbonate groups including, without limitation, methyl carbonate, 1-adamantyl carbonate, t-butyl carbonate, 4-methylsulfinylbenzyl carbonate, 2,4-dimethylpent-3-yl carbonate, vinyl carbonate, benzyl carbonate, and aryl carbamates; sulfonate groups including, without limitation, methylsulfonyl (mesylate), p-methylbenzenesulfonyl (tosylate), 4-nitrobenzene sulfonyl (nosylate), p-bromobenzenesulfonyl, trifluoromethylsulfonyl (triflate), 2-formylbenzenesulfonate, sulfoxides, and sulfonamides; silyl groups including, without limitation, alkyl silanes and aryl silanes; phosphinates including, without limitation, dimethylphosphinyl, dimethylphosphinothioyl, and diphenylphosphinothioyl. Additionally, R and $R_1$ can be joined together in a cyclic fashion with an additional 1 to 3 carbon atoms to form a ring size from 5 to 8 carbon atoms including the protecting groups methylene, pivaldehyde acetal, acetonide, cyclohexylidene, diphenylmethylene, ethyl orthoformate, cyclic borate, and cyclic carbonate.

Particularly useful protecting groups include, without limitation, methoxy, straight or branched alkyl $_{C1-C4}$, isopropyl, t-butyl, benzyl and its derivatives such as paramethoxy benzyl, acetate, pivaloate, benzoate and its derivatives such as paramethoxy benzoate, carbonate derivatives such as methyl carbonate, benzyl carbonate, tert-butyl carbonate, cyclic derivatives such as methylene and cyclic carbonate, and acetals such as tetrahydropyran and tetrahydrofuran. It should be recognized that a great variety of protecting groups could be used in the practice of the invention, although not necessarily with equivalent results.

Typically, the hydroxyl protecting groups would also work as carboxylic protecting groups. Useful carboxylic protecting groups include, without limitation, straight or branched alkyl groups from 1 to 4 carbon atoms, such as methyl, ethyl, allyl, t-butyl, and isopropyl; alkyl esters and thio esters including, without limitation, methoxymethyl ester, methylthiomethyl ester, tetrahydropyranyl ester, S-t-butyl ester, phenacyl ester, and N-phthalimidomethyl ester; benzyl esters including, without limitation, o-nitrobenzyl, p-nitrobenzyl, p-methoxybenzyl, diphenylmethyl, 4-sulfonobenzyl, and 2,4,6-trimethylbenzyl; 2-(p-toluenesulfonyl)ethyl ester, cinnamyl ester, triphenylmethyl ester, 9-anthrylmethyl ester, piperonyl ester; and ortho ester; amides including, without limitation, N,N-dimethyl amide and piperidinyl.

Amine protecting groups that are useful in the invention, much like hydroxyl protecting groups, prevent unwanted reactions towards the amine group, are not affected by reaction conditions, do not interfere with reactions on other portions of the molecule, and are easily removed at the end of the reaction scheme or at any other time that is appropriate. It is also desirable that the protecting group will help enhance reactions by increasing yield or selectivity.

Useful amine protecting groups include, without limitation, carbamates such as tert-butyl carbamate, methyl carbamate, 9-fluorenylmethyl carbamate, 1,1 dimethylpropynyl carbamate, 1-methyl-1-phenylethyl carbamate, 1-methyl-1-(4-biphenyl)ethyl carbamate, 1,1-dimethyl-2-haloethyl carbamate, 1,1-dimethyl-2 cyanoethyl carbamate, t-butyl carbamate, cyclobutyl carbamate, 1-methylcyclobutyl carbamate, 1-adamantyl carbamate, vinyl carbamate, allyl carbamate, cinnamyl carbamate, 8-quinolyl carbamate, N-hydroxypiperidinyl carbamate, 4,5-diphenyl-3-oxazolin-2-one, benzyl carbamate, p-nitrobenzyl carbamate, 3,4-dimethoxy-6-nitrobenzyl carbamate, 5-benzisoxazolylmethyl carbamate, 9-anthrylmethyl carbamate, diphenylmethyl carbamate, isonicotinyl carbamate, and S-benzyl carbamate; ureas including, without limitation, N'-phenylaminothiocarbonyl; amides and cyclic amines including, without limitation, formyl, acetyl, N-o-nitrophenylacetyl, N-o-nitrophenoxyacetyl, N-acetoacetyl, N-3-phenylpropionyl, N-2-methyl-2-(o-nitrophenoxy)propionyl, N-2-methyl-2-(o-phenylazophenoxy)propionyl, N-o-nitrocinnamoyl, N-picolinoyl, N-(N'-acetylmethionyl), N-benzoyl, N-phthaloyl, and N-dithiasuccinoyl; N-aryl and N-alkyl amines including, without limitation, N-allyl, N-phenylacyl, N-3-acetoxypropyl, N-methoxymethyl, N-benzyloxymethyl, N-pivaloyloxymethyl, N-tetrahydropyranyl, N-benzyl, N-di(p-methoxyphenyl)methyl, N-triphenylmethyl, N-(p methoxyphenyl)diphenylmethyl, N-di(p-methoxyphenyl)phenylmethyl, N-diphenyl-4-pyridylmethyl, and N-2-picolyl-N'-oxide; imine and enamine derivatives including, without limitation, N,N'-isopropylidene, N-benzylidene, N-salicylidene, and N-(5,5-dimethyl-3-oxo-1-cyclohexenyl); N-boranes including N-diphenyl boronic acid derivatives; N-sulfonates and sulfenates including, without limitation, N-beneze sulfenyl, N-2,4,6-trimethylbenzenesulfonyl, N-toluene sulfonyl, N-benzene sulfonyl, N-trifluoromethylsulfonyl, and N-phenacylsulfonyl; N-phosphinyl groups including, without limitation, N-diphenylphosphinyl and N-dimethylthiophosphinyl; N-oxide, and N-nitro. Exemplary amine protecting groups include, without limitation, N-Boc, N-formyl, N-acetyl, and N-benzoyl.

Typically, asymmetric hydrogenation catalysts are transition metal complexes with chiral ligands. The most widely used chiral catalysts include rhodium, ruthenium and iridium complexes of phosphine ligands. Some of the most useful phosphine ligands include, without limitation, BINAP, BPPM, DEGPHOS, DIOP, DIPAMP, CHIRAPHOS, SKEWPHOS, DUPHOS, BoPhoz, CnrPHOS, SYNPHOS, MeO-BIPHEP, XYLIPHOS, and BPE. It should be understood that a variety of different catalysts could be used with the invention provided that they have excellent reactivity and asymmetrically add hydrogen to produce the desired enantiomer in high enantiomeric excess (ee), typically, about 90% ee or greater. It is also desirable to keep catalyst loading to a minimum. Typically, in the interest of reducing costs, catalyst loading should be kept below 10 mole percent. Additionally, depending upon need, the catalyst can be chosen to produce either the S or R enantiomer.

As should be apparent from the above disclosure, the invention would also provide a useful and efficient method for synthesizing analogs of L-Dopa and related compounds such as L-Tyrosine, M-Tyrosine, and in particular fluorolabeled tyrosine derivatives.

EXAMPLE 1

2-t-Butoxycarbonylamino-3-(2-fluoro-4,5-dimethoxy-phenyl)-propionic acid methyl ester Step a: synthesis of 2-tert-butoxycarbonylamino-3-(2-fluoro-4,5-dimethoxyphenyl)-acrylic acid ethyl ester. To a stirred solution of 2-fluoro-4,5-dimethoxy benzaldehyde (1.0 g, 5.4 mmol) and 1,1,3,3-tetramethylguanadine (0.9 g, 8.1 mmol) in chloroform (10 mL) is added tert-butoxycarbonylamino-(dimethoxy-phosphoryl)-acetic acid ethyl ester (1.7 g 5.4 mmol) dropwise at room temperature under a $N_2$ atmosphere. The resulting solution is stirred overnight. The solution is concentrated in vacuo and the resulting product is redissolved in chloroform (20 mL) and ethyl acetate (20 mL) and washed with water (30 mL). The pH is lowered to 6 by the addition of HCl (10% solution). The phases are separated and the organic phase is washed with water (30 mL). The combined aqueous phases are concentrated in vacuo to dryness to afford 2.1 g (100%) of a white solid. $^1$H NMR is consistent with theory.

In step b, the olefin intermediate is dissolved in ethyl acetate/methanol (1/1, 40 mL) with heating. The solution is charged to a glass pressure vessel together with (S,S)-Et-DUPHOS-Rh (15 mg, 0.2 mol %). After 4 vacuum/hydrogen cycles, the vessel is pressurized to an initial pressure of 30 psi. The mixture is cooled to room temperature and then is redissolved using heat. This process is repeated several times. The mixture is left overnight at room temperature. The reaction is allowed to continue for 16 hours. TLC and $^1$H NMR analysis indicate about 50% conversion of the starting material. The reaction mixture is concentrated to dryness and purified by chromatography on silica gel. The hydrogenation process is repeated using (S,S)-Et-DUPHOS-Rh (30 mg, 0.4 mol %). After two hours the reaction is stopped and TLC analysis indicated that the conversion is complete. The reaction mixture is filtered though Celite, concentrated to dryness and purified on silica gel to afford 3 g (93%) of an amorphous solid. Chiral HPLC analysis indicates that the mixture of l to d isomers is 98.5:1.5 (97% ee).

Synthesis of F-Dopa

Step (c): synthesis of (2S)-2-amino-3-(2-fluoro-4,5-dihydroxy-phenyl)-propionic acid. HBr (10 mL, 48% water solution) is added to the reaction product of step (b). The reaction is heated in an oil bath for 5 hours. LC/MS analysis indicates complete consumption of the starting material. The reaction mixture is concentrated to dryness and the structural data indicates that the product is F-Dopa. MS: Calculated for $C_9H_{10}FNO_4$: 215.06; found: 216 (M+H), 238 (M+H), 214 (M−H). $^1H$ NMR (300 MHz, $C_2D_6SO$) δ: 2.87–2.98 (2H, m), 3.95 (1H, s), 6.52–6.62 (2H, m), 8.23 (3H, s), 8.84 (1H, s), 9.35 (1H, s), 13.74 (1H, s).

EXAMPLE 2

Synthesis of $^{18}$F-DOPA Precursor

Step a: synthesis of iodo olefin intermediate. To a stirred solution of dimethoxyiodo benzaldehyde (1.6 g, 5.4 mmol) and 1,1,3,3-tetramethylguanadine (0.9 g, 8.1 mmol) in chloroform (10 mL) is added tert-butoxycarbonylamino-(dimethoxy-phosphoryl)-acetic acid ethyl ester (1.7 g 5.4 mmol) dropwise at room temperature under a $N_2$ atmosphere. The resulting solution is stirred overnight. The solution is concentrated in vacuo and the resulting product is redissolved in chloroform (20 mL) and ethyl acetate (20 mL) and washed with water (30 mL). The pH is lowered to 6 by the addition of HCl (10% solution). The phases are separated and the organic phase is washed with water (30 mL). The combined aqueous phases are concentrated in vacuo to dryness to afford a white solid.

In step b, the olefin intermediate is dissolved in ethyl acetate/methanol (1/1, 40 mL) with heating. The solution is charged to a glass pressure vessel together with (S,S)-Et-DUPHOS-Rh (15 mg, 0.2 mol %). After 4 vacuum/hydrogen cycles, the vessel is pressurized to an initial pressure of 30 psi. The mixture is cooled to room temperature and then is redissolved using heat. This process is repeated several times. The mixture is left overnight at room temperature. The reaction is allowed to continue for 16 hours. TLC and $^1H$ NMR analysis indicate about 50% conversion of the starting material. The reaction mixture is concentrated to dryness and purified by chromatography on silica gel. The hydrogenation process is repeated using (S,S)-Et-DUPHOS-Rh (30 mg, 0.4 mol %). After two hours the reaction is stopped and TLC analysis indicated that the conversion is complete. The reaction mixture is filtered though Celite, concentrated to dryness and purified on silica gel to afford an amorphous solid.

Step c: removal of the methoxy groups. Into a dry 100 ml one-necked round bottom flask is added the dimethoxy derivative (2.54 g, 5.3 mmol) and anhydrous dichloromethane (40 mL). The reaction flask is cooled to −78° C. and $BBr_3$ (1 M in $CH_2Cl_2$, 19 mL, 27.8 g, 111 mmol) is added to the flask. The mixture is stirred for 30 minutes and then at room temperature for 30 minutes. The reaction is then poured onto ice water (100 mL) and stirred for 30 minutes at room temperature. The two layers are separated with a separatory funnel. The solids leftover are dissolved in acetonitrile, and washed with brine and $CH_2Cl_2$. The combined organic layers are dried ($MgSO_4$), filtered and concentrated to dryness to afford a solid.

Step d: addition of the Boc protecting groups. Into a dry 100 ml one-necked round bottom flask is added the catechol derivative (2.16 g, 4.8 mmol) and anhydrous DMF (30 mL). The solution is cooled to 0° C. Triethylamine is added (1.5 mL, 10.5 mmol) and the reaction color changes from yellow to dark brown. After stirring for 15 minutes, di-tert-butyl-dicarbonate (3.1 g, 14.3 mmol) in DMF (10 mL) is added using an addition funnel over 10 minutes. The reaction is stirred overnight at room temperature. The reaction mixture is poured onto brine and extracted into $Et_2O$. The combined organic layers are washed with water (5×'s), dried ($MgSO_4$), filtered and concentrated to dryness. The crude product is purified on silica gel using 4:1 $Et_2O$:hexane as the eluent to afford the product.

Step e: formation of the stannylated precursor. Into a dry 100 mL one-neck round bottom flask containing the reaction product of step (d) (1.11 g, 1.7 mmol) is added dried, degassed (via argon sparge) 1,4-dioxane (25 mL) upon which the solution becomes homogeneous. Hexamethylditin (1.5 mL, 3.4 mmol) is added under argon via a syringe followed by the addition of Pd (0) tetrakis triphenylphosphine catalyst (0.1 g) forming a yellow solution. The reaction is heated at reflux for 5 hours upon which a black precipitant forms, which indicates completion of the reaction. If a black precipitant does not form after 5 hours, additional hexamethylditin is added (3.4 mmol). The reaction mixture is filtered and concentrated to dryness. The residue is purified on silica gel using 2.5 $Et_2O$:hexane as the eluent to afford the precursor.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A compound having the following formula:

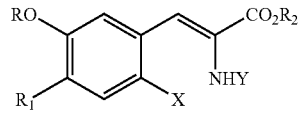

wherein R is a methyl group; $R_1$ is methoxy; $R_2$ is selected from the group consisting of an alkyl having 1 to 4 carbon atoms, and benzyl; Y is selected from the group consisting of t-butyloxycarbonyl, formyl, acetyl and benzoyl; and X is a halogen.

2. The compound according to claim 1, wherein X is selected from the group consisting of fluorine, bromine, chlorine, and iodine.

3. The compound according to claim 1, wherein X is fluorine.

4. The compound according to claim 1, wherein $R_2$ is alkyl having from 1 to 4 carbon atoms.

5. The compound according to claim 1, wherein Y is t-butyloxycarbonyl.

6. The compound according to claim 1, wherein the compound is -2-tert-butoxycarbonylamino-3-(2-fluoro-4,5-dimethoxy-phenyl)-acrylic acid ethyl ester.

* * * * *